United States Patent
Macnaughtan et al.

(10) Patent No.: US 12,082,586 B2
(45) Date of Patent: *Sep. 10, 2024

(54) BLEACH COMPOSITIONS

(71) Applicant: The Clorox Company, Oakland, CA (US)

(72) Inventors: Marisa Macnaughtan, Pepper Pike, OH (US); Nipa Modi, Pleasanton, CA (US); Thomas Fahlen, Pleasanton, CA (US); Wenyu Zhang, Pleasanton, CA (US); Ashley Joseph, Manhattan, KS (US); Timothy Mui, Pleasanton, CA (US)

(73) Assignee: THE CLOROX COMPANY, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/222,331

(22) Filed: Jul. 14, 2023

(65) Prior Publication Data

US 2023/0354815 A1 Nov. 9, 2023

Related U.S. Application Data

(60) Continuation of application No. 17/096,816, filed on Nov. 12, 2020, now Pat. No. 11,737,465, which is a division of application No. 16/182,415, filed on Nov. 6, 2018, now Pat. No. 10,986,841.

(51) Int. Cl.
| | | |
|---|---|---|
| A01N 59/00 | (2006.01) | |
| A01N 25/02 | (2006.01) | |
| A01N 25/30 | (2006.01) | |
| A61L 2/18 | (2006.01) | |
| C11D 1/62 | (2006.01) | |
| C11D 1/72 | (2006.01) | |
| C11D 1/75 | (2006.01) | |
| C11D 1/835 | (2006.01) | |
| C11D 3/48 | (2006.01) | |

(52) U.S. Cl.
CPC ............ *A01N 59/00* (2013.01); *A01N 25/02* (2013.01); *A01N 25/30* (2013.01); *A61L 2/18* (2013.01); *C11D 1/62* (2013.01); *C11D 1/72* (2013.01); *C11D 1/75* (2013.01); *C11D 1/8355* (2013.01); *C11D 3/48* (2013.01)

(58) Field of Classification Search
None
See application file for complete search history.

(56) References Cited

U.S. PATENT DOCUMENTS

| | | |
|---|---|---|
| 3,749,672 A | 7/1973 | Golton et al. |
| 3,929,678 A | 12/1975 | Laughlin et al. |
| 3,985,668 A | 10/1976 | Hartman |
| 4,259,217 A | 3/1981 | Murphy |
| 5,462,689 A | 10/1995 | Choy et al. |
| 5,821,214 A | 10/1998 | Weibel |
| 5,908,707 A | 6/1999 | Cabell et al. |
| 5,988,371 A | 11/1999 | Paley et al. |
| 6,001,187 A | 12/1999 | Paley et al. |
| 6,022,840 A | 2/2000 | Weibel |
| 6,036,789 A | 3/2000 | Weibel |
| 6,068,820 A | 5/2000 | De Guzman |
| 6,162,371 A | 12/2000 | Rees et al. |
| 6,228,824 B1 * | 5/2001 | Gorlin .................. C11D 17/003 510/435 |
| 6,245,361 B1 | 6/2001 | Merritt |
| 6,448,215 B1 | 9/2002 | Grande et al. |
| 6,471,974 B1 | 10/2002 | Rees et al. |
| 6,649,581 B1 | 11/2003 | Lalle et al. |
| 6,825,159 B2 | 11/2004 | Man et al. |
| 6,827,792 B2 | 12/2004 | Cervero et al. |
| 6,866,145 B2 | 3/2005 | Richards et al. |
| 6,998,379 B1 | 2/2006 | Costagliola |
| 7,008,600 B2 | 3/2006 | Katsigras et al. |
| 7,070,737 B2 | 7/2006 | Bains et al. |
| 7,390,775 B2 | 6/2008 | Rees et al. |
| 7,592,301 B2 | 9/2009 | Smith et al. |

(Continued)

FOREIGN PATENT DOCUMENTS

| | | |
|---|---|---|
| AU | 7054287 A | 9/1987 |
| AU | 2000043983 | 11/2000 |

(Continued)

OTHER PUBLICATIONS

Examiner Interview Summary Record (PTOL-413) Mailed on Sep. 28, 2022 for U.S. Appl. No. 17/096,852, 2 page(s).
Final Office Action received for U.S. Appl. No. 16/911,234, mailed on Mar. 22, 2023, 8 pages.
Final Office Action received for U.S. Appl. No. 17/096,852, mailed on Jul. 14, 2022, 12 pages.
Non-Final Office Action received for U.S. Appl. No. 16/911,234, mailed on Oct. 11, 2022, 6 pages.
Non-Final Office Action received for U.S. Appl. No. 17/096,816, mailed on Oct. 18, 2022, 10 pages.

(Continued)

*Primary Examiner* — Melissa S Mercier
(74) *Attorney, Agent, or Firm* — Workman Nydegger

(57) ABSTRACT

Sanitizing and disinfecting compositions with relatively low levels of free available chlorine, with good effectiveness against microbes. The composition may include less than 0.5% by weight hypochlorite or other free available chlorine level, at least one nonionic or zwitterionic surfactant, with a pH from 8 to 12.5. The composition is characterized by an R value of greater than 0 (e.g., greater than 0.5, or equal to 1), where R is defined as the sum of the concentration of any nonionic, zwitterionic, and cationic surfactants divided by the total surfactant concentration (and total surfactant concentration may include any surfactant aids). The compositions may exhibit at least a 3-log reduction in *M. bovis* or *C. diff* population within 10 minutes (e.g., 4-6 minutes).

20 Claims, No Drawings

(56) References Cited

U.S. PATENT DOCUMENTS

| | | |
|---|---|---|
| 7,807,118 B2 | 10/2010 | Green et al. |
| 7,967,220 B2 | 6/2011 | Hansen et al. |
| 8,066,444 B2 | 11/2011 | Rippl et al. |
| 8,318,654 B2 | 11/2012 | Hoffman et al. |
| 8,642,054 B2 | 2/2014 | Green |
| 8,701,880 B2 | 4/2014 | Noel |
| 8,755,114 B1 | 6/2014 | Tanner et al. |
| 8,765,114 B2 | 7/2014 | Scheuing et al. |
| 8,859,481 B2 | 10/2014 | Clark et al. |
| 8,894,907 B2 | 11/2014 | Privitera et al. |
| 8,915,359 B2 | 12/2014 | Diliberto et al. |
| 9,828,143 B2 | 11/2017 | Nathan |
| 10,279,978 B2 | 5/2019 | Diliberto et al. |
| 10,457,465 B2 | 10/2019 | Shabanova et al. |
| 10,986,841 B2 | 4/2021 | Macnaughtan et al. |
| 11,596,152 B2 | 3/2023 | Macnaughtan et al. |
| 2003/0022941 A1 | 1/2003 | Taylor et al. |
| 2003/0155549 A1 | 8/2003 | Yoshikawa et al. |
| 2005/0008575 A1 | 1/2005 | Liu |
| 2005/0008576 A1 | 1/2005 | Makansi |
| 2005/0025668 A1 | 2/2005 | Katsigras et al. |
| 2005/0155630 A2 | 7/2005 | Kilkenny et al. |
| 2005/0202491 A1 | 9/2005 | Nelson et al. |
| 2005/0282722 A1 | 12/2005 | McReynolds et al. |
| 2006/0089285 A1 | 4/2006 | Ahmed et al. |
| 2006/0278586 A1 | 12/2006 | Nalepa et al. |
| 2008/0167211 A1 | 7/2008 | Pivonka et al. |
| 2008/0305183 A1 | 12/2008 | Croud et al. |
| 2009/0016990 A1 | 1/2009 | Alberte et al. |
| 2009/0050179 A1 | 2/2009 | Kang et al. |
| 2009/0143481 A1 | 6/2009 | Man et al. |
| 2010/0305013 A1 | 12/2010 | Hanifl |
| 2011/0045187 A1 | 2/2011 | Mccloskey |
| 2013/0028990 A1 | 1/2013 | Smith et al. |
| 2013/0216293 A1 | 8/2013 | Garner et al. |
| 2013/0280349 A1 | 10/2013 | Kimler et al. |
| 2014/0117278 A1 | 5/2014 | Cawlfield et al. |
| 2014/0134224 A1 | 5/2014 | Mallet et al. |
| 2014/0328946 A1 | 11/2014 | Northey |
| 2015/0030528 A1 | 1/2015 | Xu |
| 2015/0133361 A1 | 5/2015 | Scheuing et al. |
| 2015/0306266 A1 | 10/2015 | Burke et al. |
| 2017/0208812 A1 | 7/2017 | Som et al. |
| 2018/0282048 A1 | 10/2018 | Hayman et al. |
| 2018/0344122 A1 | 12/2018 | Kang et al. |
| 2018/0361175 A1 | 12/2018 | Xu et al. |
| 2019/0023476 A1 | 1/2019 | Shabanova et al. |
| 2019/0023477 A1 | 1/2019 | Kelley et al. |
| 2020/0063077 A1 | 2/2020 | Nolan et al. |
| 2020/0138034 A1 | 5/2020 | Macnaughtan et al. |
| 2021/0059257 A1 | 3/2021 | Macnaughtan et al. |
| 2021/0059258 A1 | 3/2021 | Macnaughtan et al. |
| 2021/0403833 A1 | 12/2021 | Mui |

FOREIGN PATENT DOCUMENTS

| | | |
|---|---|---|
| AU | 2012264486 A1 | 10/2013 |
| CN | 1242797 A | 1/2000 |
| EP | 1130083 A1 | 9/2001 |
| EP | 1281320 A1 | 2/2003 |
| EP | 1550468 A1 | 7/2005 |
| RU | 2522865 C1 | 7/2014 |
| WO | 97/43392 A1 | 11/1997 |
| WO | 98/11776 A1 | 3/1998 |
| WO | 2004/108091 A2 | 12/2004 |
| WO | 2007/065533 A1 | 6/2007 |
| WO | 2010/046142 A2 | 4/2010 |
| WO | 2013/032951 A1 | 3/2013 |
| WO | 2013/032961 A1 | 3/2013 |
| WO | 2013/171343 A2 | 11/2013 |
| WO | 2014/127713 A1 | 8/2014 |

OTHER PUBLICATIONS

Non-Final Office Action received for U.S. Appl. No. 17/096,852, mailed on Feb. 2, 2022, 10 pages.

Notice of Allowance and Fees Due (PTOL-85) Mailed on Apr. 14, 2023 for U.S. Appl. No. 17/096,816, 10 page(s).

Notice of Allowance received for U.S. Appl. No. 17/096,852, mailed on Nov. 2, 2022, 11 pages.

Pentaethylene glycol monododecyl ether Sigma-Aldrich catalog, accessed Jan. 30, 2020 (Year: 2020).

Quaternium-27, SAAPedia Surfactant, http://www.saapedia.org/en/saa/?type=detail&id=3780, Jan. 10, 2023.

Rutala et al., "Uses of Inorganic hypochlorite (Bleach) in Health-Care Facilities", clinical microbioogy review (1997) vol. 10, No. 4, pp. 597-610, http://rutalapdf.web.unc.edu/files/2015/08/Rutala-1997-Uses of-inorganic-hypochlorite-bl.pdf.

* cited by examiner

BLEACH COMPOSITIONS

CROSS-REFERENCES TO RELATED APPLICATIONS

This application is a continuation of co-pending U.S. patent application Ser. No. 17/096,816 filed on Nov. 12, 2020, which is a divisional of U.S. patent application Ser. No. 16/182,415, filed on Nov. 6, 2018, now U.S. Pat. No. 10,986,841, the disclosure of each of which is hereby incorporated by reference in its entirety.

BACKGROUND OF THE INVENTION

1. The Field of the Invention

The present invention relates to liquid compositions including active chlorine species (e.g., a hypohalite), for example, as used to sanitize, disinfect, clean, or otherwise treat a surface.

2. Description of Related Art

Sodium hypochlorite is a highly effective cleaning, bleaching and sanitizing agent that is widely used in cleaning and sanitizing various hard and soft surfaces, etc. In order to achieve efficacy against various microorganisms (e.g., particularly tuberculosis ("TB") or *Clostridium difficile* ("*C. diff*"), existing bleach compositions have typically required the inclusion of at least 0.5% bleach in the formulation, particularly in order to be effective against spores of such microorganisms. Inclusion of less bleach has not typically been reliable against such microorganisms or their spores, particularly while also providing adequate shelf life for the product.

While such existing formulations can be relatively effective against target microorganisms, the inclusion of the relatively high concentrations of hypochlorite bleach components in existing formulations results in damage to hard and soft surfaces to which such compositions are applied. In addition, the characteristic "bleach" odor associated with such compositions is also often a problem. Because of concerns over such damage and overwhelming bleach odor, healthcare workers are often hesitant to use bleach compositions for disinfection, particularly for prevention of a disease outbreak. In order to better prevent outbreaks, and rather than just react to such outbreaks, all surfaces in such a healthcare setting should be treated with the most effective composition available, but as a practical matter other considerations such as surface compatibility and overall aesthetics of the product exert a heavy influence on what compositions are used, and when.

As such, there continues to be a need for liquid compositions that could provide good microefficacy against target microorganisms, at very low active chlorine concentrations (e.g., less than 0.5% by weight), while maintaining adequate stability. Development of such compositions that would have low free active chlorine concentration, while also being stable, and exhibiting good microefficacy, would be particularly advantageous as they could be applied more broadly to a wider variety of surfaces, and would exhibit more acceptable odor and other aesthetic characteristics.

BRIEF SUMMARY OF THE INVENTION

While one may consider decreasing the amount of hypohalite (e.g., hypochlorite) or other source of free available halide (e.g., free available chlorine) in such a formulation to present a solution to the above problems, conventional wisdom teaches that decreasing the amount of hypochlorite or other free available chlorine concentration will have a large negative impact on the microefficacy of the formulation. Furthermore, while it is generally known that decreasing pH can increase microefficacy, such decreases in pH are also associated with substantially decreased shelf-stability of the formulation, particularly in the presence of organic surfactants. This presents a significant challenge to provide a formulation which would have lower hypochlorite or other free available halide concentration (e.g., less than 0.5%), while still providing at least a 12 month shelf life, and also achieving efficacy against TB and/or *C. diff* microorganisms.

Applicant has unexpectedly found that certain types of surfactants greatly affect the microefficacy of such low-level bleach formulations. For example, some classes of surfactants (e.g., nonionic and/or zwitterionic surfactants) have been found to greatly enhance microefficacy of such formulations that include less than 0.5% hypochlorite or other free available chlorine. Other classes of surfactants (e.g., anionic surfactants in particular) have been found to significantly decrease the microefficacy of such formulations including less than 0.5% hypochlorite or other free available halide (e.g., chlorine). This effect of surfactant package selection was surprisingly found to be so strong that it controlled whether the formulation passed applicable EPA TB kill tests or not, independent of hypochlorite concentration. Such discovery has allowed Applicant to provide specific formulations that include only very low levels of hypochlorite or other free available chlorine, addressing issues with odor and surface compatibility, while at the same time providing microefficacy against TB, *C. diff*, or other desired target organisms.

In one embodiment, the present invention is directed to a sanitizing or disinfecting composition that includes less than 0.5% by weight of hypohalite (e.g., hypochlorite) or other free available halide (e.g., chlorine), and at least one of a nonionic or zwitterionic surfactant. Applicant has unexpectedly discovered that surfactant selection in such compositions can be at least as important as pH or other characteristics for driving stability and microefficacy. Applicant has found that inclusion of nonionic and/or zwitterionic surfactants in particular may greatly enhance microefficacy, and allow for some reduction in pH, while maintaining desired stability. Anionic surfactants have been found by Applicant to actually interfere with the ability to provide such results. For example, Applicant has discovered that by selecting the appropriate surfactant package, the concentration of hypohalite or other free available halide (e.g., chlorine) may be reduced, pH of the composition may be adjusted somewhat downward, while at the same time maintaining a desired level of microefficacy and stability. This provides a composition that exhibits improved aesthetics (e.g., odor) and surface compatibility, while still being effective against TB, *C. diff*, or other target microbes.

As such, the composition may include less than 0.5% by weight of free available halide (e.g., chlorine), and at least one of a nonionic or zwitterionic surfactant, where the composition has a pH from 8 to 12.5. The composition may have an R value that is greater than 0 (e.g., at least 0.5, or equal to 1), where R value is defined as the sum of the concentration of "good" nonionic, zwitterionic, and cationic surfactants (or chaeotropes) divided by total surfactant (including any chaeotropes, and/or any surfactant aids) concentration. The term "surfactant" is used herein broadly, for simplicity, and includes such chaeotropes or other components included principally for reducing surface tension. The composition may exhibit at least a 3-log reduction against one or both of the TB causing bacteria *Mycobacterium bovis* or *C. diff* within 10 minutes (e.g., 2-10 minutes, 3-7 minutes, or 3-5 minutes).

Such compositions advantageously include less sodium hypochlorite or other free available halide than typical existing formulations, e.g., often only 0.4% or less (e.g., 0.2% to 0.3%), so as to be less likely to cause unwanted surface damage, or exhibit an undesirable "bleach" odor during use. Such compositions may thus exhibit increased compatibility so as to be more useful across a wide variety of environments and uses.

Another embodiment is directed to a stable sanitizing or disinfecting composition including from 0.05% to less than 0.5% (e.g., 0.2% to 0.3%) by weight of hypochlorite or other free available chlorine, at least one nonionic or zwitterionic surfactant, where the R value as defined above is greater than 0, where the composition has a pH from 8.5 to 11.8, and where the composition exhibits at least a 3-log reduction in one or both of *M. bovis* or *C. diff* within 10 minutes. The composition may be free of anionic surfactants.

Another embodiment is directed to a ready-to-use sanitizing or disinfecting composition including from 0.05% to less than 0.5% by weight of a hypochlorite, at least one nonionic or zwitterionic surfactant, where the composition has an R value equal to 1, where the composition is free of anionic surfactants, and where the composition has a pH from 9 to 11.5. The composition exhibits at least a 3-log reduction in one or both of *M. bovis* or *C. diff* within 4 to 6 minutes.

Further features and advantages of the present invention will become apparent to those of ordinary skill in the art in view of the detailed description of preferred embodiments below.

DETAILED DESCRIPTION OF THE PREFERRED EMBODIMENTS

I. Definitions

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising," which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." The term "disinfect" may generally refer to the elimination of many or all pathogenic microorganisms on surfaces with the exception of bacterial endospores. The term "sterilize" may refer to the complete elimination or destruction of all forms of microbial life and which is authorized under the applicable regulatory laws to make legal claims as a "sterilant" or to have sterilizing properties or qualities.

As used herein, the term "substrate" is intended to include any material that is used to clean an article or a surface. Examples of cleaning substrates include, but are not limited to nonwovens, sponges, films and similar materials which in some embodiments can be attached to a cleaning implement, such as a floor mop, handle, or a hand held cleaning tool, such as a toilet cleaning device. In an embodiment, the substrate may be a wipe.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage are in weight percent (based on 100 weight percent active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting that 1.0% by weight corresponds to 10,000 ppm.

II. Introduction

The present inventors have surprisingly found that the choice of surfactants used in a surfactant package can be just as important, if not more so, to microefficacy and/or to stability, as pH, or even free available halide (e.g., chlorine) concentration. For example, it has been recognized for some time that at relatively higher pH values, bleach compositions are more stable, all else being equal. In addition, it has been recognized that microefficacy is higher at relatively lower pH values, all else being equal. For example, such is believed to be the case because the equilibrium hypochlorous acid concentration increases at relatively lower pH, and hypochlorous acid is a more potent oxidant in killing microbes than is hypochlorite ion.

While such effect of pH on microefficacy and stability has previously been recognized, no major effect associated with surfactant package selection has been so recognized. For example, it has previously been believed that choice of surfactant(s) had little if any impact on stability or microefficacy, other than that at high pH (e.g., particularly 12 and higher), many organic surfactants are unstable, and react with the hypochlorite or other free available chlorine, making formulation of a stable bleach composition at such pH values quite difficult. Applicant has now discovered that at least for compositions including only low levels of hypochlorite or other free available halide oxidant (e.g., less than 0.5%, less than 0.45%, less than 0.4%, or less than 0.35%) there is a surprisingly strong correlation between the choice of certain surfactants, and microefficacy and/or stability. The recognition of such correlation has allowed Applicant to formulate low-level bleach compositions that can be equally effective and stable as previous formulations, but while including significantly less sodium hypochlorite or other source of free available chlorine or other halide oxidant. The inclusion of less oxidant renders such formulations far more compatible for use on various surfaces which previously were not routinely treated with hypochlorite containing bleach compositions, out of fear that damage to applied surfaces would result. Similarly, because the concentration of free available chlorine is far lower, such compositions exhibit far less "bleach" odor, making them far more aesthetically appealing for use in healthcare and other environments.

In particular, Applicant has discovered that anionic surfactants are not particularly suitable, and actually result in decreased stability and/or microefficacy, at such low hypochlorite or other free available chlorine levels. The use of nonionic and/or zwitterionic surfactants has been discovered to be particularly suitable, for excellent stability and microefficacy, at very low free available chlorine concentrations. Cationic surfactants may also be used, e.g., in combination with a nonionic and/or zwitterionic surfactant.

By way of further explanation, because of the stability issues described above, such bleach compositions have typically been formulated at a pH of 12 or higher, e.g., by adding significant quantities of sodium hydroxide or other strong hydroxide bases to the compositions, while particular care is taken to ensure that any surfactants added are stable at such conditions. In addition to reduced microefficacy at such high pH values (but good stability), such very high pH compositions can be highly caustic due to the very high pH.

The present compositions address many of such issues, providing compositions that include very low levels of hypochlorite or other free available chlorine while still exhibiting desired characteristics relative to stability and microefficacy.

III. Exemplary Compositions a. Free Available Chlorine or Other Halide Oxidant The compositions advantageously include a component capable of providing a desired relatively low level of free available chlorine or other halide oxidant. While "free available chlorine" and "hypochlorite" are generally used herein when describing the bleach oxidant component, for purposes of simplicity it will be appreciated that a wide variety of other halides can be used, in addition to chlorine oxidizing compounds. For example, analogous compounds based on bromine are often also suitable for use. As such, use of the terms hypochlorite and free available chlorine is meant to encompass analogous hypohalites and similar halide oxidants. Examples of suitable halide oxidants include, but are not limited to alkaline metal salts and/or alkaline earth metal salts of hypochlorous acid, alkaline metal salts and/or alkaline earth metal salts of hypobromous acid, hypochlorous acid, hypobromous acid, solubilized chlorine or other solubilized halide, solubilized chlorine dioxide, acidic sodium chlorite, chlorine-dioxide generating compounds, active chlorine generating compounds, or any other source of free chlorine or other halide oxidant.

Hypohalites refer to salts of hypohalous acids. Hypochlorites and hypochlorous acid may be particularly preferred, although other hypohalites and hypohalous acids (e.g., hypobromites, hypobromous acid, etc.) may also be suitable for use. The salts may be alkali metal or alkaline earth metal salts of a hypohalous acid (e.g., hypochlorous acid), including combinations of salts, or combinations of a salt and an acid. Specific examples of hypohalites include sodium hypochlorite, potassium hypochlorite, calcium hypochlorite, magnesium hypochlorite, lithium hypochlorite, and combinations thereof. Analogous hypobromites and other hypohalites may also be suitable for use.

In an embodiment, the halide oxidant component (broadly referred to herein as hypohalite or other free available halide oxidant) may be present in an amount from 0.1% to less than 0.5% by weight of the composition, from 0.1% to 0.45% by weight of the composition, from 0.1% to 0.4% by weight of the composition, from 0.2% to 0.4% by weight of the composition, or from 0.2% to 0.3% by weight of the composition. In some embodiments, the hypohalite or other free available halide oxidant level may be less than 0.45%, less than 0.4%, or less than 0.35% by weight of the composition.

b. Surfactants

Surfactants have typically be included in bleach compositions to improve the wetting or spreading ability of the formulation on surfaces through a reduction in surface tension, to better solubilize oily soils, or to aid in solubilizing aesthetic components such as fragrances. In the past, the conventional approach has been to formulate such compositions at pH 12 or greater, and to take particular care to select a surfactant that is stable under such extreme pH conditions. Applicant has surprisingly discovered that hypochlorite or other free available chlorine concentration can be significantly reduced (e.g., to less than 0.5%), and that under such conditions, surfactant selection becomes the major driver to stability and/or microefficacy of the formulation. For example, Applicant has found that choice of surfactant package can affect stability and microefficacy just as strongly as pH, or concentration of hypochlorite, which discovery has been surprising. Such discovery has allowed Applicant to reduce the concentration of hypochlorite, improving surface compatibility and aesthetics, while still delivering a desired level of stability and/or microefficacy, e.g., by providing the composition with a particular surfactant package tailored to provide such results.

In particular, while previously little attention has been paid to any effect that surfactant may have on stability and/or microefficacy, Applicant has found that the type of surfactant selected for inclusion in the formulation can be very important to achieving the desired stability and/or microefficacy characteristics, particularly at the very low levels of hypochlorite or other free available chlorine as contemplated herein. By way of example, previous compositions employed any surfactant, as selected from various anionic, nonionic, cationic, amphoteric, or zwitterionic surfactants, including mixtures of classes of surfactants, so long as it was stable at the typical high pH value (e.g., 12+), and intentionally provided relatively high levels of hypochlorite or other free available chlorine to ensure microefficacy. For example, conventional wisdom holds that microefficacy and stability can be achieved by selecting a surfactant that is stable at high pH, by keeping pH at 12 or higher, and by providing a high level of hypochlorite to the formulation.

There has been no real development of low-level hypochlorite or other free available chlorine compositions that would exhibit low "bleach" odor, improved surface compatibility, and at the same time provide similar 1-year stability while also exhibiting similar microefficacy against TB, C. diff, or other target microbes. There was no appreciation that at such low levels of hypochlorite, the type of surfactant may actually become the primary driver of stability and/or microefficacy. Applicant has discovered that anionic surfactants have a strong negative effect on stability and/or microefficacy, at the low concentrations of hypochlorite or other free available chlorine as contemplated herein. Nonionic and/or Zwitterionic surfactants have been found to have a strong positive effect on stability and/or microefficacy within such low-level bleach formulations. As such, the present compositions advantageously include nonionic and/or zwitterionic surfactants. If included, the concentration of anionic surfactants is limited. At least some embodiments according to the present invention include no anionic surfactants at all. Cationic surfactants may optionally be present.

Examples of nonionic surfactants include, but are not limited to, alcohol ethoxylates, alcohol propoxylates, alkyl phosphine oxides, alkyl glucosides and alkyl pentosides, alkyl glycerol esters, alkyl ethoxylates, and alkyl and alkyl phenol ethoxylates of all types, poly alkoxylated (e.g. ethoxylated or propoxylated) $C_6$-$C_{12}$ linear or branched alkyl phenols, $C_6$-$C_{22}$ linear or branched aliphatic primary or secondary alcohols, and $C_2$-$C_8$ linear or branched aliphatic glycols. Block or random copolymers of $C_2$-$C_6$ linear or branched alkylene oxides may also be suitable nonionic surfactants. Capped nonionic surfactants in which the terminal hydroxyl group is replaced by halide; $C_1$-$C_8$ linear, branched or cyclic aliphatic ether; $C_1$-$C_8$ linear, branched or cyclic aliphatic ester; phenyl, benzyl or $C_1$-$C_4$ alkyl aryl ether; or phenyl, benzyl or $C_1$-$C_4$ alkyl aryl ester may also be used. Sorbitan esters and ethoxylated sorbitan esters may also be useful nonionic surfactants. Other suitable nonionic surfactants may include mono or polyalkoxylated amides of the formula $R^1CONR^2R^3$ and amines of the formula $R^1NR^2R^3$ wherein $R^1$ is a $C_5$-$C_{31}$ linear or branched alkyl group and $R^2$ and $R^3$ are $C_1$-$C_4$ alkyl, $C_1$-$C_4$ hydroxyalkyl, or alkoxylated with 1-3 moles of linear or branched alkylene oxides. Biosoft 91-6 (Stepan Co.) is an example of an alkyl ethoxylate (or alcohol ethoxylate) having a methylene chain length of $C_9$ to $C_{11}$ with an average of 6 moles of ethoxylation. An example of an alcohol ethoxylate is ECOSURF EH-9, which is more specifically an ethylene oxide-propylene oxide copolymer mono(2-ethylhexyl) ether, available from Sigma-Aldrich.

Alkylpolysaccharides that may be suitable for use herein are disclosed in U.S. Pat. No. 4,565,647 to Llenado, having a linear or branched alkyl, alkylphenyl, hydroxyalkyl, or hydroxyalkylphenyl group containing from 6 to 30 carbon atoms and a polysaccharide, e.g., a polyglycoside, hydrophilic group containing from 1.3 to 10 saccharide units. Suitable saccharides include, but are not limited to, glucosides, galactosides, lactosides, and fructosides. Alkylpolyglycosides may have the formula: $R^2O(CnH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 10.

Fatty acid saccharide esters and alkoxylated fatty acid saccharide esters may also be suitable for use in the present invention. Examples include, but are not limited to, sucrose esters, such as sucrose cocoate, and sorbitan esters, such as polyoxyethylene(20) sorbitan monooleate and polyoxyethylene(20) sorbitan monolaurate.

Phosphate ester surfactants may also be suitable. These include mono, di, and tri esters of phosphoric acid with $C_4$-$C_{18}$ alkyl, aryl, alkylaryl, alkyl ether, aryl ether and alkylaryl ether alcohols (e.g. disodium octyl phosphate).

Zwitterionic surfactants may be employed. Many such zwitterionic surfactants contain nitrogen. Examples of such include amine oxides, sarcosinates, taurates and betaines. Examples include $C_8$-$C_{18}$ alkyldimethyl amine oxides (e.g., octyldimethylamine oxide, lauryldimethylamine oxide (also known as lauramine oxide), and cetyldimethylamine oxide), $C_4$-$C_{16}$ dialkylmethylamine oxides (e.g. didecylmethylamine oxide), $C_8$-$C_{18}$ alkyl morpholine oxide (e.g. laurylmorpholine oxide), tetra-alkyl diamine dioxides (e.g. tetramethyl hexanane diamine dioxide, lauryl trimethyl propane diamine dioxide), $C_8$-$C_{18}$ alkyl betaines (e.g. decylbetaine and cetylbetaine), $C_8$-$C_{18}$ acyl sarcosinates (e.g. sodium lauroylsarcosinate), $C_8$-$C_{18}$ acyl $Ci$-$C_6$ alkyl taurates (e.g. sodium cocoylmethyltaurate), $C_8$-$C_{18}$ alkyliminodipropionates (e.g. sodium lauryliminodipropionate), and combinations thereof. Lauryl dimethyl amine oxide (Ammonyx LO) myristyl dimethyl amine oxide (Ammonyx MO), decylamine oxide (Ammonyx DO) are examples of suitable zwitterionic surfactants, available from Stepan Co.

Cationic surfactants may optionally be included, e.g., in combination with a nonionic and/or zwitterionic surfactant. Examples of cationic surfactants include, but are not limited to monomeric quaternary ammonium compounds, monomeric biguanide compounds, and combinations thereof. Suitable exemplary quaternary ammonium compounds are available from Stepan Co. under the tradename BTC (e.g., BTC 1010, BTC 1210, BTC 818, BTC 8358). Any other suitable monomeric quaternary ammonium compound may also be employed. BTC 1010 and BTC 1210 are described as didecyl dimethyl ammonium chloride and a mixture didecyl dimethyl ammonium chloride and n-alkyl dimethyl benzyl ammonium chloride, respectively. Examples of monomeric biguanide compounds include, but are not limited to chlorhexidine, alexidine and salts thereof. Cetyl ($C_{16}$) trimethylammonium chloride (CETAC) and pentyl ($C_5$) trimethyl ammonium chloride are specific examples of cationic quaternary ammonium surfactants.

Additional exemplary cationic surfactants include alkyltrimethylammonium, alkylpryidinium, and alkylethylmorpholinium salts, in which the alkyl group contains 4 to 18 carbon atoms, alternatively 12 to 16 carbon atoms. The alkyl chains may be linear or branched or contain an aryl group. The counterion may be, but is not limited to, chloride, sulfate, methylsulfate, ethylsulfate, or toluene sulfonate. Other suitable cationic surfactants include dialkyldimethyl ammonium salts, in which the alkyl groups each contain 4 to 12 carbon atoms such as dioctyldimethyl ammonium chloride. Other suitable cationic surfactants may have two quaternary ammonium groups connected by a short alkyl chain such as N-alkylpentamethyl propane diammonium chloride. In the above cationic surfactants the methyl substituents can be completely or partially replaced by other alkyl or aryl substituents such as ethyl, propyl, butyl, benzyl, and ethylbenzyl groups, for example octyldimethylbenzyl ammonium chloride and tetrabutylammonium chloride.

The present formulations preferably avoid the use of anionic surfactants. Non-limiting examples of such surfactants to be avoided include alkyl sulfates (e.g., $C_8$-$C_{18}$ linear or branched alkyl sulfates such as sodium lauryl sulfate (SLS), and sodium tetradecylsulfate), alkyl sulfonates (e.g., $C_6$-$C_{18}$ linear or branched alkyl sulfonates such as sodium octane sulfonate and sodium secondary alkane sulfonate, alkyl ethoxysulfates, fatty acids and fatty acid salts (e.g., $C_6$-$C_{16}$ fatty acid soaps such as sodium laurate), and alkyl amino acid derivatives. Other examples may include sulfate derivatives of alkyl ethoxylate propoxylates, alkyl ethoxylate sulfates, alpha olefin sulfonates, $C_6$-$C_{16}$ acyl isethionates (e.g. sodium cocoyl isethionate), $C_6$-$C_{18}$ alkyl, aryl, or alkylaryl ether sulfates, $C_6$-$C_{18}$ alkyl, aryl, or alkylaryl ether methylsulfonates, $C_6$-$C_{18}$ alkyl, aryl, or alkylaryl ether carboxylates, sulfonated alkyldiphenyloxides (e.g. sodium dodecyldiphenyloxide disulfonate), and the like.

More specific examples of particularly suitable nonionic and/or zwitterionic surfactants include lauryl dimethyl amine oxide (Ammonyx LO), also known as lauramine oxide, myristyl dimethyl amine oxide (Ammonyx MO), decylamine oxide (Ammonyx DO), other amine oxides, any betaines, linear alcohol ethoxylates, alcohol propoxylates, alkyl polyglucosides, and combinations thereof. Cationic surfactants, such as any quaternary ammonium chloride may optionally be present.

Specific examples of anionic surfactants to be avoided include sodium lauryl sulfate (SLS), linear alkylbenzene sulfonate (LAS), any other sulfates, sulfonates, disulfonates, and any carboxylate fatty acids, particularly where such include alkyl groups have more than 1, more than 2, more than 3, more than 4, or 8 or more carbon atoms in the alkyl group.

While such anionic surfactants are generally to be avoided, some embodiments may include a surfactant aid, which surfactant aid may technically be anionic. An example of such a suitable surfactant aid is an aromatic sulfonate, such as sodium xylene sulfonate ("SXS"). Although SXS is anionic, its presence as a surfactant aid is acceptable in at least some embodiments. For example, the xylene group of SXS is a far shorter "tail" than a lauryl or other typical long alkyl or other group such as is present in SLS, or LAS, where the alkyl benzene includes an ethyl or typically longer (e.g., $C_3$ or greater, $C_4$ or greater, $C_6$ or greater, etc.) alkyl chain. As a practical matter, while SXS may provide some anionic charge, due to its smaller structure, it can protect certain surfactants, while exhibiting little if any real surfactant activity itself, such that it is termed a surfactant aid, rather than a surfactant, herein. Other aromatic sulfonates may similarly serve as acceptable surfactant aids, particularly where they have no alkyl groups larger than a methyl group (e.g., sodium mesitylene sulfonate "SMS", or the like).

In one embodiment, the surfactants may be selected based on green or natural criteria. For example, there is an increasing desire to employ components that are naturally-derived, naturally-processed, and biodegradable, rather than simply being recognized as safe. Such "natural surfactants" may be produced using processes perceived to be more natural or ecological, such as distillation, condensation, extraction, steam distillation, pressure cooking and hydrolysis.

Additional examples of various surfactants are given in U.S. Pat. No. 3,929,678 to Laughlin and Heuring, U.S. Pat. No. 4,259,217 to Murphy, and U.S. Publication No. 2013/0028990. The above patents and applications are each herein incorporated by reference in their entirety.

The formulation may have an R value, where R is the sum of the concentration of any "good" surfactants (e.g., nonionic, zwitterionic, and cationic surfactants) divided by total surfactant concentration (including surfactant aids). For example, 0.05 wt % of LO divided by the sum of 0.05 wt % LO and 0.1 wt % SXS equals an R value of 0.33. Such R value may be greater than 0, such as from 0.01 to 1, from 0.1 to 1, from 0.5 to 1, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.9, or equal to 1 (i.e., all surfactants included are "good", with no anionic surfactants or surfactant aids included). In an embodiment, the value of R may be equal to 1, but for the inclusion of a surfactant aid (such as SXS). As described herein, while SXS technically decreases the R value, the practical effect of its inclusion does not negate the microefficacy and/or stability benefits associated with otherwise high R values. In other words, a composition that includes an R value that is less than 1 (e.g., 0.5) solely because of the inclusion of an anionic surfactant aid exhibits far better microefficacy and/or stability as compared to a similar composition of the same R value, but where the decrease in R value is because of the inclusion of an anionic surfactant having a long alkyl group, such as SLS.

In an embodiment, the R values may also refer to the "best" nonionic and/or zwitterionic surfactants, absent any "acceptable" cationic surfactants that may be included. For example, while cationic surfactants are acceptable, they are used in combination with a nonionic and/or zwitterionic surfactant. As such, the total of nonionic and/or zwitterionic surfactants may account for at least 30%, at least 35%, at least 40%, at least 45%, at least 50%, at least 55%, at least 60%, at least 65%, at least 70%, at least 75%, at least 80%, at least 85%, or at least 90% of total surfactants.

In an embodiment, surfactant concentration may typically be far lower than many other bleach formulations, e.g., given the low level of other active ingredients in the formulation. For example, total surfactant concentration may range from 0.001% by weight to 1% by weight, from 0.01% to 0.5% by weight, from 0.01% by weight to 0.1% by weight. The ratio of surfactant to hypohalite or other free available halide oxidant may be from 1:1 to 100:1, from 3:1 to 50:1, from 5:1 to 20:1 or from 5:1 to 15:1.

The composition may have a low viscosity, e.g., such as up to 1000 cps, or 1 to 100 cps.

c. Other Adjuvants

In addition to the oxidant and the surfactant(s), a wide range of optional adjuvants may be present. For example, buffers, oils, fragrances, solvents, pH adjusters (e.g., acids or bases), builders, silicates, preservatives and chelating agents, including but not limited to EDTA salts, GLDA, gluconates, 2-hydroxyacids and derivatives, glutamic acid and derivatives, trimethylglycine, etc. may be included.

Dyes and colorants may be present. Thickeners may be present.

Enzymes may be present, e.g., particularly when the formulations are tuned for use as laundry detergents or as cleaners for kitchen and restaurant surfaces, or as drain openers or drain maintenance products.

Water-miscible solvents may be present in some embodiments. Lower $C_1$-$C_4$ alcohols (e.g., ethanol, t-butanol), ethylene glycol, propylene glycol, glycol ethers, and mixtures thereof with water miscibility at 25° C. may be present in some embodiments. Other embodiments may include no lower alcohol (e.g., particularly ethanol or methanol) or glycol ether solvents. Where such solvents are present, some embodiments may include them in only small amounts, for example, of not more than 5%, not more than 3%, not more than 2%, not more than 1%, or not more than 0.5% (e.g., from 0.01% to 0.5%) by weight.

Water-immiscible oils or solvents may be present, being solubilized into the surfactant micelles. Among these oils include those added as fragrances. Preferred oils are those that are from naturally derived sources, including the wide variety of so-called essential oils derived from a variety of botanical sources. Formulations intended to provide antimicrobial benefits, coupled with improved overall sustainability may advantageously comprise quaternary ammonium compounds and/or monomeric biguanides such as water soluble salts of chlorhexidine or alexidine in combination with essential oils such as thymol and the like, preferably in the absence of water-miscible alcohols.

Silicates, builders, chelating agents, preservatives, fragrances, and any other adjuvants may be included in appropriate, effective amounts. In some embodiments, such levels may be from 0.01 to 10% by weight, or from 0.1 to 5% by weight, or from 0.1 to 1% by weight.

Suitable buffers include those materials capable of controlling ultimate solution pH and which themselves resist reaction with the oxidant and remain in sufficient concentration to control the pH. Suitable buffers further include those buffers that are non-consumable with respect to action by the hypochlorite or other free available chlorine oxidant. In addition, suitable buffers may have an acid dissociation constant (Ka) at 20° C. in the range from $1 \times 10^{-2}$ to $1 \times 10^{-12}$, from $1 \times 10^{-3}$ to $1 \times 10^{-11}$, from $1 \times 10^{-3}$ to $1 \times 10^{-8}$, or from $1 \times 10^{-8}$ to $1 \times 10^{-12}$.

Suitable buffers may include salts and/or corresponding conjugate acids and bases of the following classes of materials, and their derivatives: carbonates, bicarbonates, silicates, boric acid and borates, di- and mono-basic phosphates or phosphoric acid, monocarboxylic or polycarboxylic acids such as acetic acid, succinic acid, octanoic acid, the like, and combinations thereof. Sodium carbonate is one such specific example.

In an embodiment, the buffer, if present, may be present from 0.001% by weight to 10% by weight, from 0.01% to 5% by weight, from 0.1% by weight to 1% by weight, or from 0.1% to 0.5% by weight.

pH values for the present compositions may be greater than 7, and less than 13, such as 8 to 12.5, greater than 8, greater than 9, 10 or greater, less than 12, 8 to 12.5, 8.5 to 11.8, 9 to 11.5, or the like. Preferably pH is less than 12, which somewhat increases the variety of organic surfactants that can be used, as stable under such conditions.

Concentrated forms of the formulations may be provided which may be diluted with water by the consumer to provide solutions that are then used. Concentrated forms that suitable for dilution via automated systems, in which the concentrate is diluted with water, or in which two solutions are combined in a given ratio to provide the final use formulation are possible.

The compositions are liquids (e.g., as opposed to solid compositions). The vast majority of the composition may comprise water (e.g., at least 90%, at least 95%, at least 97%, at least 98%, or at least 99% water).

Compositions including low levels of hypochlorite or other free available chlorine, and surfactant packages as described herein may be used in a wide variety of environments where sanitization and/or disinfection is desired. Examples of such include but are not limited to cleaning, disinfection, sterilization, deodorization, mold removal, toxin and/or allergen remediation, application to surfaces that may contact food, treatment of hard surfaces, fabrics or other soft surfaces, treatment of tools or other implements in health care or other settings, glass cleaners, toilet cleaning, and the like. The compositions may be provided in various forms, e.g., as a ready-to-use dilute liquid spray, as a concentrate for dilution by the user, in an aerosol form, in a pouch, as a ready-to-use foam, ready-to-use gel, included on or within a wipe or other substrate, etc.

IV. Examples

The stability and microefficacy of various compositions were tested.

Microefficacy was tested against *C. diff* and 2 TB strains (e.g., *Mycobacterium bovis* Karlson and Lessel ATCC 35743) according to applicable EPA standard operating procedures for testing both with and without soil (e.g., SOP MB-24-03). The following testing and data was performed according to the EPA standard operating procedures for testing with soil.

Table 1 shows 24 compositions that were prepared and tested. Table 2 shows some of the characteristics of the compositions of Table 1, e.g., relating to stability and microefficacy.

TABLE 1

| Sample | NaOCl (ppm) | SLS (wt %) | LO (wt %) | SXS (wt %) | t-butanol (wt %) | silicate (wt %) | pH | Calculated R value |
|---|---|---|---|---|---|---|---|---|
| A | 2000 | — | 0.05 | 0.1 | 0.5 | — | 10.5 | 0.33 |
| B | 2000 | — | 0.05 | 0.1 | 0.1 | — | 10.5 | 0.33 |
| C | 2000 | 0.05 | — | — | 0.1 | — | 10.5 | 0 |
| D | 2000 | 0.05 | — | — | 0.5 | — | 10.5 | 0 |
| E | 3000 | 0.05 | — | 0.033 | — | — | 11 | 0 |
| F | 2000 | — | — | — | — | — | 10 | — |
| G | 2000 | 0.05 | — | — | — | — | 10 | 0 |
| H | 2000 | — | — | — | — | — | 11.6 | 0 |
| I | 2000 | 0.05 | — | — | — | — | 11.6 | 0 |
| J | 2000 | — | 0.03 | — | — | — | 10.5 | 1 |
| K | 2000 | — | 0.03 | — | 0.1 | — | 10.5 | 1 |
| L | 2000 | 0.03 | — | — | 0.1 | — | 10.5 | 0 |
| M | 2500 | — | 0.03 | — | — | — | 11 | 1 |
| N | 2500 | — | 0.03 | — | 0.1 | — | 11 | 1 |
| O | 2500 | 0.03 | — | — | — | — | 11 | 0 |
| P | 2000 | — | 0.05 | 0.1 | 0.1 | 0.25 | 10 | 0.33 |
| Q | 2000 | — | 0.05 | 0.1 | 0.1 | 0.25 | 10.5 | 0.33 |
| R | 2500 | — | 0.05 | 0.1 | 0.1 | 0.25 | 10.5 | 0.33 |
| S | 2500 | — | 0.05 | 0.1 | — | 0.25 | 10.5 | 0.33 |
| T | 2000 | — | 0.1 | 0.1 | 0.1 | 0.25 | 11 | 0.5 |
| U | 2500 | — | 0.05 | 0.1 | — | 0.25 | 11 | 0.33 |
| V | 2000 | — | 0.03 | — | — | 0.25 | 10.6 | 1 |

TABLE 1-continued

| Sample | NaOCl (ppm) | SLS (wt %) | LO (wt %) | SXS (wt %) | t-butanol (wt %) | silicate (wt %) | pH | Calculated R value |
|---|---|---|---|---|---|---|---|---|
| W | 2500 | — | 0.03 | — | — | 0.25 | 10.6 | 1 |
| X | 2000 | — | 0.05 | 0.04 | — | 0.25 | 10.6 | 0.56 |

LO = lauryl dimethyl amine oxide (Ammonyx LO)
SLS = sodium lauryl sulfate
SXS = sodium xylene sulfonate

TABLE 2

| Sample | Phase Stability | Shelf Stability | C. diff effectivity in 5 min | TB effectivity | Calculated R |
|---|---|---|---|---|---|
| A | Yes | Borderline | — | Borderline[1] | 0.33 |
| B | Yes | Borderline | — | Borderline[1] | 0.33 |
| C | Yes | Yes | — | Borderline[1] | 0 |
| D | Yes | Yes | — | Fail[1] | 0 |
| E | Yes | Yes | — | Borderline[1] | 0 |
| F | Yes | No | Pass | Fail[2] | — |
| G | Yes | No | Pass | Fail[2] | 0 |
| H | Yes | Yes | — | Fail[2] | 0 |
| I | Yes | Yes | — | Fail[2] | 0 |
| J | Yes | Borderline | Borderline | Borderline[3] | 1 |
| K | Yes | Borderline | Pass | Borderline[3] | 1 |
| L | Yes | Borderline | — | Fail[3] | 0 |
| M | Yes | Yes | Pass | Borderline[3] | 1 |
| N | Yes | Yes | Pass | Borderline[3] | 1 |
| O | Yes | Yes | — | Fail[3] | 0 |
| P | Yes | No | Pass | Pass[3] | 0.33 |
| Q | Yes | Yes | — | Fail[3] | 0.33 |
| R | Yes | Borderline | Pass | Borderline[3] | 0.33 |
| S | Yes | Borderline | Pass | Fail[3] | 0.33 |
| T | Yes | Yes | — | Borderline[3] | 0.5 |
| U | Yes | Yes | Pass | Fail[3] | 1 |
| V | Yes | Yes | Borderline | Pass[1] | 1 |
| W | Yes | Yes | Pass | Pass[1] | 1 |
| X | Yes | Yes | Fail | Pass[1] | 0.56 |

[1] TB effectivity tested at 5 minutes
[2] TB effectivity tested at 3 and 5 minutes
[3] TB effectivity tested at 7 minutes Table 2 shows the unexpectedly significant effect that the surfactant package has on microefficacy against *C. diff* and TB microbes. In particular, the testing of the above 24 formulations, and others tested by Applicant indicates that the choice of surfactant package has a greater effect on microefficacy than even pH or hypochlorite concentration. In particular, examples V and W, which had R values of 1 were particularly promising, as they exhibit phase stability, shelf stability, and effectivity against both *C. diff* and TB, at very low hypochlorite (e.g., free available chlorine) concentrations. Examples M and N, also at R values of 1, also exhibited promising results. Example T, at an R value of 0.5 also showed some promise. Those examples that had R values of 0 were characterized by lack of shelf-stability and/or poor microefficacy. At least some of those formulations that would have had an R value of 1 but for the inclusion of SXS also often showed promising results, against at least some microbes.

In evaluating the formulations, a given formulation is shelf-stable if no more than 25% of the available chlorine (e.g., hypochlorite concentration) is lost within 12 months. Such testing is routinely performed at an elevated temperature (e.g., 120° F.) on an accelerated time schedule to predict shelf-stability. For example, 28 days at 120° F. may be indicative of 1 year stability at 70° F. Details of such accelerated stability testing are disclosed in Applicant's U.S. Pat. Nos. 7,008,600 and 7,070,737, each of which is herein incorporated by reference in its entirety.

The exemplary formulations seen in Tables 1 and 2 include lauramine oxide (LO) as the non-ionic surfactant, in relatively small amounts (e.g., 0.03%, 0.05%, or 0.1%). Sodium lauryl sulfate (SLS) was used as the exemplary anionic surfactant in the tested formulations (e.g., at 0.03% or 0.05%), showing the benefits of including a surfactant package that only includes nonionic and/or zwitterionic surfactants, or at least where the R ratio is such that any anionic surfactant is a minority (or not a majority) of the total. Sodium xylene sulfonate (SXS) was used as a surfactant aid (e.g., at 0.033%, 0.04%, or 0.1%). T-butanol was used as a solvent (e.g., 0.1% or 0.5%). Some formulations also included N-sodium silicate, which serves to protect metal surfaces from damage. Other silicate salts or phosphate salts may alternatively be used for such. Such silicates or phosphates may be present in a range of up to 0.2%, up to 0.1%, or up to 0.05% by weight. Such low concentrations are preferred to minimize build-up on any treated surfaces.

With respect to chlorine concentration, chlorine may be routinely measured and/or reported as free available chlorine, combined chlorine, or total residual chlorine. Free available chlorine refers to generally 3 forms of chlorine that may be found in such formulations: (a) elemental chlorine ($Cl_2$), (b) hypochlorous acid (HOCl), and (c) hypochlorite ion ($OCl^-$). As used herein, use of the phrase "free available chlorine" for practical purposes may be the same as the hypochlorite concentration, as while some hypochlorous acid and/or dissolved $C_{12}$ may be present, the hypochlorite represents the vast majority of such free available chlorine, and it is typically a concentration or amount of hypochlorite that is added to the formulation (after which some of this forms hypochlorous acid and/or dissolved $Cl_2$) according to equilibrium. In other words, where 2500 ppm of hypochlorite is initially added to a given formulation, the free available chlorine may also be 2500 ppm. The vast majority of that amount may remain as hypochlorite, while some small fraction thereof may be converted to hypochlorous acid and/or dissolved $Cl_2$, but the formulation would continue to initially exhibit a free available chlorine concentration of 2500 ppm. Over time or during use, such components are consumed as an oxidant, in reaction, or decomposition of such components gradually occurs, reducing the free available chlorine concentration. As described above, other halides (e.g., bromine) can be understood as analogous to the above discussion of hypochlorites and free available chlorine.

As noted above, due to the stability characteristics of such hypochlorite formulations, it would be expected that the concentration of hypochlorite will gradually drop over the given 12 month shelf-life (e.g., where shelf-stable is defined as a loss of no more than 25% hypochlorite after 12 months at 70° F.). Recognizing such, the formulation as initially manufactured and sold may have a concentration that is about 25% higher than those "target" formulations shown in Tables 1-3, such that after a year of storage, the hypochlorite concentration would be as seen in such tables. For example, at the typical 2000 ppm to 3000 ppm concentrations contemplated herein, one might expect a loss of about 500 ppm of hypochlorite over such a 1 year period of time. A decomposition of 500 ppm of hypochlorite will drop the overall pH value of the formula by about 0.5 pH units, where a carbonate or other buffer is present at e.g., from 0.2% to less than 0.4%.

Table 3 shows another 24 compositions that were prepared for testing.

TABLE 3

| Sample | NaOCl (ppm) | SLS (wt %) | LO (wt %) | SXS (wt %) | EH-9 (wt %) | C10L (wt %) | BTC (wt %) | pH | R value |
|---|---|---|---|---|---|---|---|---|---|
| 3-1 | 2100 | — | — | — | — | — | — | 11.6 | — |
| 3-2 | 2100 | — | — | — | — | — | — | 10.3 | — |
| 3-3 | 2100 | 0.0508 | — | — | — | — | — | 11.6 | 0 |
| 3-4 | 2100 | 0.0508 | — | — | — | — | — | 10.3 | 0 |
| 3-5 | 2100 | — | 0.0516 | — | — | — | — | 11.6 | 1 |
| 3-6 | 2100 | — | 0.0516 | — | — | — | — | 10.3 | 1 |
| 3-7 | 2100 | — | 0.0252 | — | — | — | 0.027 | 11.6 | 1 |
| 3-8 | 2100 | — | 0.0288 | — | — | — | 0.027 | 10.3 | 1 |
| 3-9 | 2100 | — | — | — | 0.011 | — | — | 11.6 | 1 |
| 3-10 | 2100 | — | — | — | 0.0496 | — | — | 10.3 | 1 |
| 3-11 | 2100 | — | — | — | — | 0.0564 | — | 11.6 | 0 |
| 3-12 | 2100 | — | — | — | — | 0.0528 | — | 10.3 | 0 |
| 3-13 | 2100 | — | — | 0.051 | — | — | — | 11.6 | 0 |
| 3-14 | 2100 | — | — | 0.05 | — | — | — | 10.3 | 0 |
| 3-15 | 2100 | 0.0496 | — | 0.051 | — | — | — | 11.6 | 0 |
| 3-16 | 2100 | 0.0521 | — | 0.05 | — | — | — | 10.3 | 0 |
| 3-17 | 2100 | — | 0.0504 | 0.051 | — | — | — | 11.6 | 0.5 |
| 3-18 | 2100 | — | 0.0504 | 0.05 | — | — | — | 10.3 | 0.5 |
| 3-19 | 2100 | — | 0.0312 | 0.051 | — | — | 0.0304 | 11.6 | 0.55 |
| 3-20 | 2100 | — | 0.0336 | 0.05 | — | — | 0.0264 | 10.3 | 0.57 |
| 3-21 | 2100 | — | — | 0.051 | 0.0498 | — | — | 11.6 | 0.49 |
| 3-22 | 2100 | — | — | 0.05 | 0.051 | — | — | 10.3 | 0.5 |
| 3-23 | 2100 | — | — | 0.051 | — | 0.0552 | — | 11.6 | 0 |
| 3-24 | 2100 | — | — | 0.05 | — | 0.0564 | — | 10.3 | 0 |

LO = lauryl dimethyl amine oxide (Ammonyx LO)
SLS = sodium lauryl sulfate
SXS = sodium xylene sulfonate
EH-9 = ECOSURF EH-9, a nonionic alcohol ethoxylate surfactant
C10L = DOWFAX C10L, an anionic alkyldiphenyloxide disulfonate surfactant
BTC = BTC 1010, a cationic didecyl dimethyl ammonium chloride surfactant The formulations of Table 3 show various alternatives. Where the R level falls within the preferred ranges as described herein (e.g., examples 3-5 to 3-10, and 3-17-3-22), such formulations may provide effective sanitization and/or disinfection.

For EPA sporicidal testing protocols, (i.e., number of spores killed per specific amount of composition applied), because of the very low levels of hypochlorite, a point is reached where the composition runs out of hypochlorite oxidant (i.e., all the bleach has reacted) before all the spores in the test have been killed. In such a case, the surfactant package selected may not boost the overall number of spores killed, but will decrease the time in which it takes to kill a set number of spores.

Lotions for pre-moistened wipes using any of the examples described herein may be added to nonwoven substrates to produce pre-moistened wipes or other substrate cleaning devices. The ratio of lotion to substrate may be from about 0.1:1 and 10:1 by weight. Such wipes or other substrates may be employed as disinfecting wipes, or for floor cleaning in combination with various tools configured to attach to the wipe or substrate. Additional details of exemplary substrates, including non-woven substrates are found in U.S. Publication No. 2005/0155630, herein incorporated by reference in its entirety.

Without departing from the spirit and scope of the invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A sanitizing or disinfecting composition comprising:

(a) about 0.05% to about 0.5% by weight of a hypochlorite or free available halide as provided by an oxidant; and (b) at least one nonionic or zwitterionic surfactant;

(c) at least 90% water;

(d) wherein the composition has an R value that is greater than 0, where R value is defined as the sum of the concentration of any included nonionic, zwitterionic, and cationic surfactants divided by total surfactant concentration;

(e) wherein the composition has a pH from about 8 to about 12.5;

(f) wherein the sanitizing or disinfecting composition exhibits at least a 3-log reduction in at least one of an *M. bovis* or *C. diff* population within 10 minutes;

wherein the composition has a viscosity of no more than about 100 cps.

2. The composition of claim 1, wherein the pH is between about 8.5 and about 11.8.

3. The composition of claim 1, wherein the pH is between about 9 and about 11.5.

4. The composition of claim 1, wherein the at least one nonionic or zwitterionic surfactant comprises: one or more of an alkyl amine oxide, an alcohol ethoxylate, an alcohol propoxylate, or an alkyl polyglucoside.

5. The composition of claim 4, wherein the surfactant comprises at least one of lauramine oxide, decylamine oxide, or myristyl dimethylamine oxide.

6. The composition of claim 1, wherein the oxidant comprises a hypohalite.

7. The composition of claim 1, wherein the oxidant comprises a hypochlorite.

8. The composition of claim 7, wherein the hypochlorite comprises sodium hypochlorite.

9. The composition of claim 1, wherein the sanitizing or disinfecting composition exhibits at least a 3-log reduction in a *C. diff* population within 6 minutes.

10. The composition of claim 1, wherein the sanitizing or disinfecting composition exhibits at least a 3-log reduction in an *M. bovis* population within 6 minutes.

11. The composition of claim 1, wherein the R value is greater than about 0.5.

12. The composition of claim 4, wherein the surfactant comprises an alkyl polyglucoside.

13. The composition of claim 1, wherein free available chlorine as provided by the oxidant is in a range from about 0.1% to less than about 0.5% by weight.

14. The composition of claim 1, wherein free available chlorine as provided by the oxidant is in a range from about 0.1% to about 0.4% by weight.

15. The composition of claim 1, wherein free available chlorine as provided by the oxidant is in a range from about 0.2% to about 0.3% by weight.

16. A ready-to-use sanitizing or disinfecting composition comprising:
    (a) about 0.05% to less than about 0.5% weight percent of a hypochlorite;
    (b) at least one nonionic or zwitterionic surfactant; and
    (c) at least 90% water,
    (d) wherein the composition has an R value that is greater than 0, where R value is defined as the sum of the concentration of any included nonionic, zwitterionic, and cationic surfactants divided by total surfactant concentration;
    (e) wherein the composition has a pH from about 9 to about 11.5;
    (f) wherein the sanitizing or disinfecting composition exhibits at least a 3-log reduction in a *C. diff* population within 6 minutes.

17. The composition of claim 16, wherein the at least one nonionic or zwitterionic surfactant comprises one or more of an alkyl amine oxide, an alcohol ethoxylate, an alcohol propoxylate, or an alkyl polyglucoside.

18. The composition of claim 16, wherein the R value is greater than about 0.5.

19. The composition of claim 16, wherein free available chlorine as provided by the oxidant is in a range from about 0.1% to less than about 0.5% by weight.

20. The composition of claim 16, wherein free available chlorine as provided by the oxidant is in a range from about 0.1% to about 0.4% by weight.

* * * * *